United States Patent [19]

Korol

[11] Patent Number: 4,563,184
[45] Date of Patent: Jan. 7, 1986

[54] SYNTHETIC RESIN WOUND DRESSING AND METHOD OF TREATMENT USING SAME

[76] Inventor: Bernard Korol, 11908 Country Club Dr., St. Louis, Mo. 63131

[21] Appl. No.: 542,754

[22] Filed: Oct. 17, 1983

[51] Int. Cl.$^4$ .......................... C08K 5/41; C08K 5/34; C08K 5/15; C08K 5/10; A61L 15/01; A61L 15/06; A61L 15/03
[52] U.S. Cl. ..................... 604/368; 128/156; 523/111; 514/936; 514/946; 514/965; 524/104; 524/111; 524/167; 524/173; 524/233; 524/296; 524/317
[58] Field of Search ............... 523/111, 122; 128/156, 128/334, 335.5; 424/28, 33, 81; 524/173, 560

[56] References Cited

U.S. PATENT DOCUMENTS

| | | | |
|---|---|---|---|
| 3,067,096 | 12/1962 | Trace | 426/134 |
| 3,551,554 | 12/1970 | Herschler | 424/88 |
| 3,576,760 | 4/1971 | Gould | 252/403 |
| 3,576,946 | 4/1971 | Chromecek et al. | 524/558 |
| 3,577,516 | 5/1971 | Gould et al. | 424/78 |
| 3,592,936 | 7/1971 | Marcus et al. | 424/81 |
| 3,598,122 | 8/1971 | Zaffaroni | 604/897 |
| 3,598,123 | 8/1971 | Zaffaroni | 604/897 |
| 3,618,213 | 11/1971 | Shepherd . | |
| 3,731,683 | 5/1973 | Zaffaroni | 604/897 |
| 3,734,097 | 5/1973 | Zaffaroni | 604/897 |
| 3,742,951 | 7/1973 | Zaffaroni | 604/897 |
| 3,770,500 | 11/1973 | Imaoka | 428/403 |
| 3,813,466 | 5/1974 | Anderson | 424/28 |
| 3,826,619 | 7/1974 | Bratu | 422/71 |
| 3,854,480 | 12/1974 | Zaffaroni | 604/897 |
| 3,867,517 | 2/1975 | Ling | 514/456 |
| 3,868,447 | 2/1975 | Kliment | 424/81 |
| 3,896,789 | 7/1975 | Traneik | 604/307 |
| 3,916,038 | 10/1975 | Yamaguchi | 427/127 |
| 3,933,997 | 1/1976 | Hersh | 436/526 |
| 3,946,106 | 3/1976 | Chien | 424/892 |
| 3,955,566 | 5/1976 | Stoffey | 128/90 |
| 3,963,685 | 6/1976 | Abrahams | 128/156 |
| 3,970,518 | 7/1976 | Giaever | 435/239 |
| 3,981,776 | 9/1976 | Saxholm | 436/514 |
| 3,993,073 | 11/1976 | Zaffaroni | 604/891 |
| 4,012,497 | 3/1977 | Schopflin | 424/22 |
| 4,018,886 | 4/1977 | Giaever | 436/526 |
| 4,031,202 | 6/1977 | Laughlin | 424/28 |
| 4,039,501 | 8/1977 | Babcock et al. | 524/173 |
| 4,052,505 | 10/1977 | Higuchi | 424/14 |
| 4,073,291 | 2/1978 | Marvel | 128/155 |
| 4,078,568 | 3/1978 | Etes | 604/336 |
| 4,122,158 | 10/1978 | Schmitt | 424/27 |
| 4,126,503 | 11/1978 | Gardner | 156/184 |
| 4,131,650 | 12/1978 | Braumer | 424/28 |
| 4,136,162 | 1/1979 | Fuchs | 424/27 |
| 4,142,521 | 3/1979 | Konikoff | 128/82.1 |

(List continued on next page.)

FOREIGN PATENT DOCUMENTS 794031  1/1981  U.S.S.R. .

OTHER PUBLICATIONS

Polymer Handbook, Brandrup et al editors, pp. IV-34-7-357, Interscience Pub.

Primary Examiner—Veronica P. Hoke
Attorney, Agent, or Firm—Paul M. Denk

[57] ABSTRACT

A synthetic resin wound dressing (e.g., a burn wound dressing) is disclosed consisting essentially of a polymer, such as poly(2-hydroxyethylmethacrylate), referred to as PHEMA, an organic solvent, such as polyethylene glycol (PEG), and a hydrogen binding plasticizer, such as dimethylsulfoxide (DMSO). The plasticizer regulates the set-up time of the synthetic resin so that the more plasticizer present, the shorter the set-up time. The dressing may be applied to the wound site in the form of a paste for the in situ curing or setting thereof, or the dressing may be preformed and then applied to the wound site. A variety of drug agents (e.g., silver sulfadiazine) may be incorporated in the synthetic resin so as to result in the time released administration of the drug agent to the area of the skin (e.g., a burn wound site or the like) covered by the wound dressing. A method of treatment using this dressing is also disclosed.

39 Claims, 8 Drawing Figures

U.S. PATENT DOCUMENTS

| | | | |
|---|---|---|---|
| 4,144,317 | 3/1979 | Higuchi | 424/21 |
| 4,164,559 | 9/1979 | Miyata | 424/14 |
| 4,191,743 | 3/1980 | Klemm | 424/28 |
| 4,243,656 | 1/1981 | Walliczek | 424/28 |
| 4,268,497 | 5/1981 | Griffin | 424/27 |
| 4,272,510 | 6/1981 | Smith | 427/47 |
| 4,272,518 | 6/1981 | Moro et al. | 424/81 |
| 4,287,177 | 9/1981 | Nakashima et al. | 424/81 |
| 4,292,299 | 9/1981 | Suzuki | 424/16 |
| 4,294,820 | 10/1981 | Keith | 424/28 |
| 4,303,066 | 12/1981 | D'Andrea | 128/156 |
| 4,307,075 | 12/1981 | Martin | 424/28 |
| 4,310,509 | 1/1982 | Berglund | 424/28 |
| 4,342,784 | 8/1982 | Havemeyer et al. | 424/78 |

RATS SCALD BURNED 10 SECONDS 95 DEGREE CENTIGRADE.

SYNTHETIC RESIN WOUND DRESSING AND METHOD OF TREATMENT USING SAME

BACKGROUND OF THE INVENTION

This invention relates to a synthetic resin (i.e., plastic) wound dressing, and to a method or process of wound treatment wherein the dressing may optionally contain various time release medicinal or drug agents. More specifically, the wound dressing of the present invention may be applied to a wound site (e.g., a burn wound site) as a paste and allowed to set-up in place on the burn wound site or, alternatively, the wound dressing of this invention may be pre-cured and pre-formed and then applied to the wound site. The preformed material may be attached to an elastic fabric to further improve its use by preventing adherence to the overlying dressing and also preventing cracking of the burn dressing. Still further, the wound dressing and treatment method of the present invention may be used in the transdermal or topical administration of a variety of drugs.

More generally, in the standard current treatment of wounds, such as severe burn wounds, a topical medicinal agent, such as an antimicrobial agent (e.g., silver sulfadiazine or the like), is applied to a layer of gauze, and prior to the application of the gauze on the wound site, the medicated gauze is cut to the size and shape of the open wound area so as to prevent maceration of adjacent unburned or healed skin. Care is taken to protect the burn wound areas from coming into contact with one another as, for example, by placing folded gauze between burned fingers, toes, and between the ear and head, after the initial medicated gauze has been applied to the burn wound sites. Then, fluffed gauze or other bulky dressings may be applied, if it is desired to maintain warm body temperatures. A Kling wrap or the like may be used to secure the dressings in place. The patient's extremities and joints are arranged in a desired position. Typically, the dressings are changed one or more times each day, allowing the physician to observe the healing of the wound and to reapply the medicinal agent. The repeated changing of the dressing causes intense pain to the patient, risks contamination of the wound with microbial infection, disturbs the healing process, and requires considerable time of the treating physician or clinician, thus substantially increasing the cost of treatment. Such daily changing of dressings is typically required until the wound has healed, or until the wound is grafted. Often times, such periodic changing of the dressing is required for a period up to two or three weeks.

Heretofore, various burn wound treatments have been utilized in which a synthetic resin film or coating dressing is applied to the wound site as a paste so as to cure or set up in place thereby to serve as a skin covering for the burn wound lesion during the healing process. While such in situ settable synthetic resin dressings have gained wide clinical usage in burn treatment, the set-up or hardening time required by many such previous synthetic resin dressings was unduly long. Such extended set-up times required the continued attendance of the treating physician, and is often painful to the patient due to the uncomfortable position the patient must maintain during the entire dressing or paste set-up period.

One such in situ plastic wound bandage is disclosed in U.S. Pat. No. 4,272,518 to Moro et al, which is a settable paste consisting of a polymer (e.g., a three-dimensional, 2-hydroxyethylmethacrylate), and an inert, normally liquid solvent (e.g., polyethylene glycol). While this plastic wound bandage paste worked well for its intended purpose in that a non-tacky, homogeneous, occlusive film was formed on the surface of the wound, relatively long and unpredictable set-up times (in some instances up to an hour) resulted when useful ratios of solvent vis-a-vis the polymer were mixed. Also, in many instances, the resulting film bandage formed on the wound site became brittle and was subject to cracking or splitting, especially upon movement of the patient, thus rendering the plastic film substantially ineffective as a barrier against personnel, patient or environmentally transmitted bacteria and the like.

Various pastes made from organic solvent soluble polymers of hydroxyalkylacrylates and methylacrylates (known as HEMA pastes) are described in U.S. Pat. No. 3,868,447 to Kliment for use as a sound energy transfer media in ultrasound diagnostic testing, as a carrier of local anesthestics in dental surgery, or as a protective layer over dental fillings during setting.

U.S. Pat. No. 3,575,946 to Chromechek et al discloses various solvent soluble polymers of ethylene glycol, a monomethacrylate and monoacrylate contaminated with various percentages of dimethacrylates or bisacrylates.

A water soluble polymer of hydroxyalkylacrylate or methacrylate is disclosed in U.S. Pat. No. 3,576,760 to Gould et al in which a variety of drugs, pesticides, flavoring agents and fragrances can be entrapped.

In U.S. Pat. No. 3,557,516 to Gould et al, a spray-on bandage is disclosed in which a hydrophilic water insoluble polymer, such as a hydroxy lower alkylacrylate or ethylacrylate, is disclosed as a high boiling point plasticizer or solvent, is sprayed onto the wound area site so as to form an in situ bandage.

Environmental wound barrier dressings or hydrophilic, water insoluble, organic soluble polymers of hydroxyalkyl methacrylate or acrylate are disclosed in U.S. Pat. No. 3,963,685 to Abrahms, and are commercially available under the trademark HYDRON from Abbott Laboratories of Chicago, Ill. While other such barrier dressings have met with commercial acceptance, these dressings may have a tendency to crack, thus necessitating repair of the cracks or fissures therein.

Reference may also be made to the following U.S. patents for examples of various tapes, bandages, or other dressings for carrying a supply of time-released, medicinal agents which are topically applied to the skin or wound site for transdermal absorption: U.S. Pat. Nos. 3,896,789, 3,955,566, 4,012,497, 4,073,291, 4,122,158, 4,136,162, 4,164,559, 4,191,743, 4,268,497, 4,292,299, 4,310,509, and 4,307,075.

Walliczek, U.S. Pat. No. 4,243,656, discloses a biosynthetic polymeric burn wound dressing containing a polyacrylate polymer, humectants, such as glycerol, gelatin, and water, which is supplied to the wound site.

In U.S. Pat. No. 3,551,554 to Herchler, a method of enhancing tissue penetration of a variety of topically applied physiologic active agents not contained in a solid delivery system is disclosed by topically applying the agent to the skin, together with a relatively high concentration (e.g., 50–90%) of dimethylsulfoxide (DMSO).

Keith et al, U.S. Pat. No. 4,294,820, discloses a polymeric diffusion matrix for the sustained transdermal delivery of a medicinal (e.g., phenylephrine). Like the prior patent to Herchler, Keith et al disclose the use of high concentrations of DMSO as a skin absorption facilitator or skin penetration enhancer.

SUMMARY OF THE INVENTION

Among the many objects and features of the present invention may be noted the provision of a wound dressing, a method of wound treatment, and a system for the administration of a variety of medicinal or therapeutic drug agents which, in the treatment of burn wounds or the like, eliminates the necessity for the daily (or more often) changing of wound dressings;

The provision of such a dressing, wound treatment method, and system which continuously releases therapeutically effective concentrations of established antimicrobials or other medicinal agents over extended periods of time directly to the burn wound site without the necessity of having to remove the wound dressing;

The provision of such a dressing, wound treatment method, and system in which a synthetic resin dressing is applied directly to the burn wound site for extended periods of time (e.g., up to 14 days or more), so as to serve as an artificial barrier against nosocomial infection;

The provision of such a dressing, wound treatment method, and system in which the wound dressing may be applied in a non-hardened (non-set) condition so as to constitute an in situ applied dressing, or in which the dressing may be preformed and preset at a location remote from the patient and then applied to the wound site;

The provision of such a dressing, wound treatment method, and system in which the wound dressing is substantially transparent so that the treating physician may visually observe the condition in or around the wound during treatment without the necessity of removing the dressing from the wound site, thus violating the microbial barrier protection afforded to the wound site by the occlusive dressing;

The provision of such a dressing, wound treatment method, and system in which the synthetic resin dressing may optionally be applied and adhered to a two dimensional, stretchable carrier sheet or substrate forming a laminated preparation so as to enhance the structural integrity of the dressing;

The provision of such a dressing, wound treatment method, and system in which the above-mentioned wound dressing is flexible so it will readily conform to the contours of the wound site, and so that it will permit at least limited mobility of the patient without causing cracking or the formation of fissures in the dressing;

The provision of such a dressing, wound treatment method, and system wherein the set-up time of the synthetic resin wound dressing of this invention directly applied as a paste may be selectively varied between a matter of several seconds up to about 45 minutes so as to give the treating physician or clinician applying the dressing sufficient time to work the dressing as it is applied to the wound site, but yet does not require the patient to remain in uncomfortable positions for extended periods of time merely to allow the barrier wound dressing to set-up or to cure;

The provision of such a dressing, wound treatment method, and system which is compatible with a wide range of medicinal agents, including antibiotics, cardiovascular drugs, anti-inflammatory drugs, hormones, anticonvulsants, analgesics, and germicides, for the time release of the medicinal agent to the wound site or to normal skin for the topical or transdermal application of a selective drug;

The provision of such a dressing, wound treatment method, and system in which gastrointestinal effects on orally administered drugs are eliminated and in which the drug may be applied directly to a desired site on the body;

The provision of such a dressing, wound treatment method, and system in which the dressing, whether applied as a paste to the wound site and permitted to cure in place, or whether precured and preformed and applied as a bandage, the dressing remains flexible, elastic, retards cracking, remains adhesive, remains transparent and is compatible with a wide range of drugs which may be incorporated therein; and The provision of such a dressing, wound treatment method, and system which is relatively easy to use, which lessens pain experienced by the patient, which provides an effective anti-microbial barrier, which need not be frequently (e.g., daily) replaced, and which facilitates healing of the patient.

Other objects and features of this invention will be in part apparent and in part pointed out hereinafter.

Briefly stated, the method of this invention for treatment of a patient, such as a burn wound patient or the like, comprises applying a dressing to the skin (i.e., to the burn wound site). The dressing is a synthetic resin, occlusive film or sheet, comprising a settable hydrophilic, water swellable polymer, a non-toxic water miscible liquid organic solvent, and a hydrogen binding plasticizer additive. The polymer, solvent, and plasticizer additive, when mixed together, form a settable paste. The polymer is preferably a poly(2-hydroxyethylmethacrylate) (referred to as PHEMA), or other hydroxymethylacrylate, or hydroxyacrylate, or the like. The organic solvent is preferably polyethylene glycol (referred to as PEG) or the like, and the plasticizer additive is preferably dimethylsulfoxide (referred to as DMSO). The percentage by weight of the synthetic resin constituted by the polymer ranges between about 30–55%, the percentage by weight of the synthetic resin constituted by the solvent ranges between about 20–60%, and the percentage by weight of the synthetic resin constituted by the plasticizer additive ranges up to about 15%–20% by weight of the dressing.

BRIEF DESCRIPTION OF THE DRAWINGS

Corresponding reference characters indicate corresponding parts throughout the several views of the drawings.

DESCRIPTION OF PREFERRED EMBODIMENTS

Figure 1:
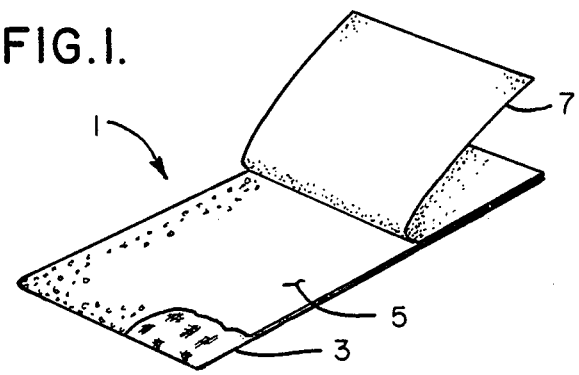
FIG. 1 is a perspective view of a preformed wound dressing of the present invention as it is applied to a biaxially stretchable substrate, with a backing sheet covering the dressing material, the backing sheet being shown in a partially peeled-away condition.

Generally, the synthetic wound dressing of the present invention comprises a resin of varying concentrations of biologically compatible, non-toxic, hydrophilic, water insoluble, water swellable polymer, such as poly(2-hydroxyethylmethacrylate), referred to as PHEMA. Additionally, the resin comprises an inert, water soluble, organic liquid solvent, such as polyethylene glycol (referred to as PEG) or the like, and a hydrogen binding plasticizer additive, such as dimethylsulfoxide (referred to as DMSO). It has been found that the formulation of the resin of this invention, consisting essentially of PHEMA, PEG, and DMSO and referred to collectively as DIMAC, can be altered so as to control the set-up time of the resin from almost simultaneous with mixing (e.g., several seconds) up to about 45 minutes or longer, depending on the relative concentration of DMSO. Further, in its broader aspects, this invention includes a method and system of treatment in which the above-mentioned synthetic resin wound dressing can be preloaded with a variety of effective therapeutic agents which are released into wounds or tissue over prolonged periods.

The wound dressing of this invention may be prepared to form a paste spreadable directly on the wound site (or on a predetermined location of the body) so as to constitute an in situ applied wound dressing. In in situ wound dressings, the set-up time of the settable preparation is of significance because it is essential that the clinician have an adequate amount of time to properly spread the paste over the wound site such that the paste maintains a workable consistency, and yet, after the paste has been applied, such that the patient does not have to maintain a predetermined position for a relatively long length of time so as to faciliate set-up of the paste without causing cracking thereof. It will be appreciated that within the broader aspects of this invention the relative amount of plasticizer provided in the synthetic resin wound dressing of the present invention may be selectively varied so that the amount of set-up time for the wound dressing can be predetermined.

However, it will be also understood that the synthetic resin wound dressing of the present invention may be preformed such that the wound dressing bandage in an already adherent state is applied to the wound site rather than as a spreadable paste. More specifically, referring to FIG. 1, such a preformed wound dressing bandage is illustrated in its entirety by reference character 1. This preformed wound dressing 1 is shown to comprise a substrate 3, preferably of a biaxially stretchable fabric-like material. For example, such a bidirectional stretchable material made of nylon and Lycra is available from Tweave, Inc., Norton, Mass., under the trade designation or Style #901. This bidirectional, stretchable backing material has been found particularly advantageous because it allows ready handling of the wound dressing applied thereto, and it permits the wound dressing to be wrapped with gauze or other bandages so as to hold the wound dressing in a desired location on the patient's body without the wrapping gauze coming in contact with or becoming embedded in the synthetic wound dressing.

Further, as illustrated in FIG. 1, a layer of the synthetic wound dressing 1 of the present invention is applied to the front face of substrate 3 with the layer of synthetic wound dressing being indicated by reference character 5. To protect the wound dressing coating 5 applied to substrate 3 prior to use and to maintain it in an aseptic condition, a plastic film backing sheet 7 is applied to the synthetic wound dressing coating 5 and is slightly adhered to substrate 3. As shown in FIG. 1, prior to use, the backing sheet 7 is peeled from the wound dressing so as to expose the wound dressing coating 5 on substrate 3, thus making the bandage ready for application on the wound site. Substrates 3 and 7 may extend beyond the wound dressing 5 to provide a non-adhesive tab permitting easy handling of the dressing after removal of the cover film 7 without touching the active sticky surface 5.

While the inclusion of the DMSO plasticizer as a component of the formulation of the synthetic resin wound dressing of the present invention has heretofore been described as primarily aiding in giving predictability to the set-up time of the synthetic resin wound dressing, it has been found, even in the cases of preformed wound dressing bandages, such as shown in FIG. 1, that the inclusion of DMSO (or other plasticizers) as a component of the formulation for the synthetic wound dressing coating 5 on the bandage, has a beneficial effect in that it is believed that the DMSO plasticizer results in a solidification or curing of the polymer system of the synthetic resin wound dressing such that there is a progressive gelling of the resin mixture preceding the actual set-up of the mixture. The term "set-up" is defined as the time between the mixing of the components of the synthetic resin wound dressing into a paste and the time an occlusive, non-tacky film appears on the surface of the paste with little or no adhesiveness to the touch. Generally, at the time of set-up, the resin still will have a pliable consistency. When no drug or medicament has been added, the paste in its "set-up" condition will have a semi-opaque character.

Then, depending on the relative concentration of the components of the synthetic resin system, a progressively developing transparency of the resin film will result with an increase in elasticity and rebound of the resin, and the surface of the resin will generally have a significantly increased surface adhesiveness resulting from the reactions of the added DSMO. Generally, these last-described changes and physical characteristics of the resin system require about 5 to 10 times longer to develop than is required for the initial "set-up" to occur. This delayed process of developing a transparent film with an increase in elasticity, rebound and surface adhesiveness is referred to as curing.

Accordingly, those skilled in the art will recognize that even in preformed wound dressings, as shown in FIG. 1, the presence of the DMSO plasticizer permits the synthetic resin material of the present invention to readily be applied to substrate 3 in a predetermined thickness when in its set-up mode, when the wound dressing resin has little or no adhesiveness to the touch. Then, as the curing phenomena progresses, as the wound dressing resin becomes progressively more adhesive, the wound dressing coating will have already been applied to substrate 3, thus eliminating the necessity of spreading or otherwise handling the adhesive coating.

Still further, it has been found that the inclusion of DMSO (or other plasticizer) in the synthetic resin wound dressing of the present invention, whether an in situ wound dressing paste or a preformed wound dressing bandage 1 (as shown in FIG. 1), significant improvements in the physical and functional characteristics of the wound dressing of this present invention utilizing DMSO plasticizers are exemplified, including increased flexibility, elasticity, resistance to cracking, integral microbial barrier protection, and adhesiveness.

As heretofore stated, the synthetic resin wound dressing of the present invention is comprised essentially of a water soluble, water swellable, non-toxic hydrophilic polymer and an inert, normally liquid organic solvent, and a hydrogen binding plasticizer. In its preferred embodiment, the polymer and the liquid organic solvent together with an effective amount of the plasticizer (i.e., an amount capable of varying the set-up time and of improving the physical and functional characteristics of the resulting wound dressing) should be capable of forming a settable synthetic resin paste. Further, as heretofore described, the polymer is preferably a three-dimensional poly(2-hydroxyethylmethacrylate) (PHEMA), the liquid organic solvent is preferably polyethylene glycol (PEG), having a molecular weight of about 200–2,000, and the hydrogen binding plasticizer is preferably dimethylsulfoxide (DMSO). In most of the examples that follow, polyethylene glycol having a molecular weight of about 400–800, was used. However, it will be understood that a variety of other polymers and liquid solvents may be utilized. Reference may be made to the prior patent to Moro et al (U.S. Pat. No. 4,272,518) for a more complete listing of alternative polymers and solvents which may be utilized in accordance with this invention. The disclosure of U.S. Pat. No. 4,272,518 is, for the purposes of brevity, herein incorporated by reference.

As previously mentioned, the synthetic resin wound dressing of the present invention may be applied directly to the wound site as a settable paste, thus constituting an in situ wound dressing, or, alternatively, the synthetic resin wound dressing of the present invention may be preformed and applied as a bandage, generally as illustrated in FIG. 1. Further, in accordance with the broader aspects of this invention, various active medicaments may be incorporated in the synthetic resin wound dressing of the present invention for topical or transdermal drug application over a sustained period of time. The dressing may be directly applied to the wound or it may be prepared as a laminated preparation fixed to a nylon/Lycra backing.

Figure 7:
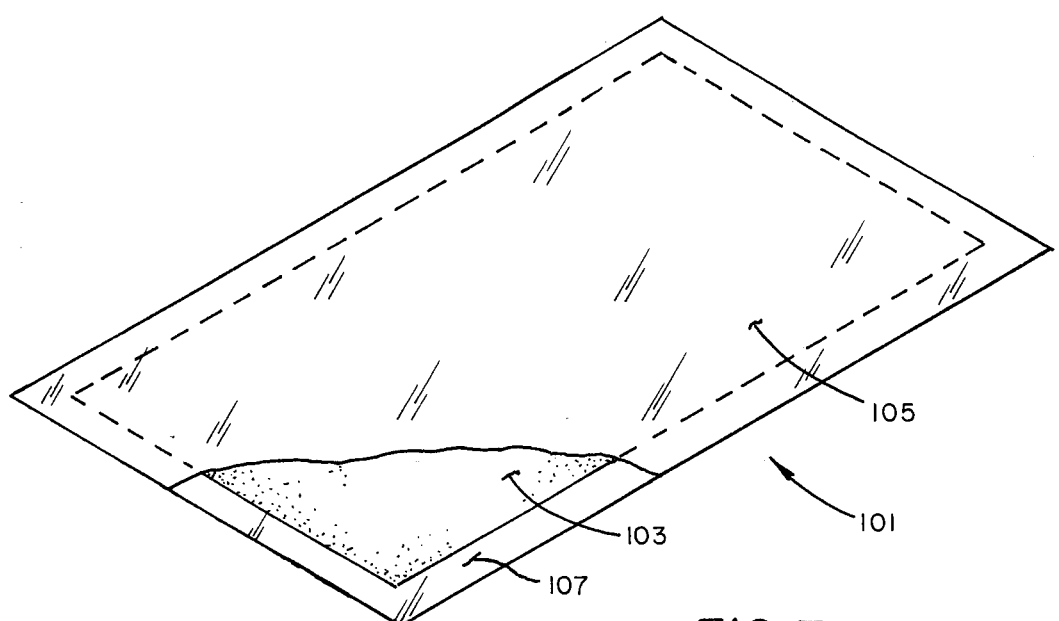
FIG. 7 is a perspective view of a preformed wound dressing of the present invention sheathed between two backing sheets with the wound dressing and the backing sheets being substantially transparent.

Referring to FIG. 7, another embodiment of a preformed synthetic resin wound dressing of the present invention is indicated in its entirety by reference character 101. More specifically, wound dressing 101 comprises a pad 103 of the synthetic resin of this invention (i.e., DIMAC) of a predetermined thickness (e.g., 0.5 to 1.0 mm.). The pad is covered by upper and lower backing sheets 105 and 107, respectively, of thin, transparent plastic film sealed around their margins so as to maintain the pad in an aseptic condition. In use, one of the backing sheets may be peeled from pad 103 to expose a surface of the pad and the pad may be applied to a burn wound site. Because the pad and the remaining backing sheet are transparent, the clinician may visually observe the wound site through the pad without the requirement of having to remove the wound dressing and thus violating the microbial barrier provided by the wound dressing. It will be understood that if a medicament (e.g., silver sulfadiazine) is added to the DIMAC resin (referred to as DIMAC/Plus), the resulting resin may become semi-opaque. Where desired, both substrate 3 and cover film 7 may be removed. The remaining dressing 5 may be left in place or may be secured by means of bandages or other devices.

EXAMPLE 1

Seven different formulations of synthetic resin wound dressing of the present invention were compounded, mixed, and evaluated for set-up time, appearance, flexibility, maintenance of film integrity. For example, the set-up time was determined from the time when the solvent was mixed with the polymer and the plasticizer. In each of the following seven formulations, a one-minute mixing period was utilized. The mixture containing components of synthetic resin wound dressing of the present invention were poured into a plastic mixing cap, and the end of the set-up time period was defined as the time from initiation of mixing of the components of synthetic resin wound dressing of the present invention to the time when it was possible to gently remove the synthetic resin wound dressing of the present invention in the form of a pad from the plastic cap cover.

When mixin these formulations, the solvent was polyethylene glycol 400, the polymer was poly(2-hydroxyethylmethacrylate) from a HYDRON burn dressing kit (Lot. No. 177003B), commercially available from Abbott Laboratories, of Chicago, Ill., and the dimethylsulfoxide (DMSO) plasticizer was obtained from Sigma Aldrich, of St. Louis, Mo., Lot. No. TD1327PD.

The mixing procedure was to add the solvent and plasticizer to the polymer at 0-time and then to stir the components for one minute and to apply to the inside of a plastic cap cover. The proportions of the plasticizer (DMSO), the solvent (PEG), and the polymer (PHEMA), as a percentage by weight of the total weight of synthetic resin wound dressing of the present invention, together with observed set-up time is presented in Table I as follows:

TABLE I

| Formula # | DMSO % | PEG % | PHEMA % | Set-Up Time |
|---|---|---|---|---|
| I | 0.0 | 47.06 | 52.94 | greater than 90 minutes |
| II | 6.0 | 41.12 | 52.87 | 15–20 minutes |
| III | 8.75 | 39.92 | 51.33 | 5–10 minutes |
| IV | 11.34 | 38.79 | 49.94 | 1–5 minutes |
| V | 5.67 | 44.39 | 49.94 | 10–15 minutes |
| VI | 2.84 | 47.19 | 49.97 | 25 minutes |
| VII | 4.26 | 45.79 | 49.95 | 15 minutes |

It was observed that as the amount of DMSO was increased, the set-up time of the resulting wound dressing decreased.

EXAMPLE 2

In this exmple, four of the formulations from Example 1 (i.e., Formulas I, V, VI and VII), together wwith two additional formulations (i.e., Formulas VIII and IX) were mixed generally in the manner heretofore described in Example 1, and the set-up time for the formulations was observed. In this case, the paste was applied to the forearm of the experimenter at various times after mixing. The set-up time after application was determined with the time to set up being initiated at the time the paste is applied to the forearm. The set-up time was defined as the time after application until the appearance of an occlusive, non-tacky film. Formulations of these various pastes, together with the set-up time and the time after mixing when applied to the forearm, are set forth in Table II.

TABLE II

Formula #I: 0.0% DMSO: 47.06% PEG: 52.94% PHEMA
After Mix:   2   4   6   8   10  15  20 (minutes)
Set-up time: 22  22  21  14  15  15  10 (minutes)
Formula #V: 5.67% DMSO: 44.39% PEG: 49.94% PHEMA
After Mix:   1   3   5 (minutes)
Set-up time: 3   2   2 (minutes)
Formula #VI: 2.84% DMSO: 47.19% PEG: 49.97% PHEMA
After Mix:   1   2   5   10 (minutes)
Set-up time: 9   8   5   3 (minutes)
Formula #VII: 4.26% DMSO: 45.79% PEG: 49.95% PHEMA
After Mix:   2   5   7 (minutes)
Set-up time: 5   5   3 (minutes)
Formula VIII: 4.54% DMSO: 45.51% PEG: 49.95% PHEMA
After Mix:   2   4   6   8 (minutes)
Set-up time: 4   3   2   1 (minutes)
Formula IX: 3.41% DMSO: 46.63% PEG: 49.96% PHEMA
After Mix:   2   3   4   5   6   8   10 (minutes)
Set-up time: 7   6   5   4   4   3   2 (minutes)

The sum of the set-up time and after mix application time was relatively constant for each formulation. The set-up time decreased as the DMSO content increased.

EXAMPLE 3

This example, five additional formulations (i.e., Formulas X–XIV) synthetic resin wound dressing of the present invention were mixed and were formed into sheets of predetermined thickness. Specifically, the PEG solvent and the DMSO plasticizer wee introduced into the requisite amount of PHEMA polymer powder, in the quantities by weight, as indicated in Table III, at zero mix time, and mixing was continued for one minute. The resulting paste was then poured onto flat 4-inch by 4-inch (10.2 by 10.2 cm.) sheet of synthetic resin film, available under the trademark PLASTIPAC, having a thickness of approximately 0.001 inch. Then, shims of either 0.5 or 1.0 mm. were placed along the edges of plastic sheets and a top sheet of the plastic film material was positioned on top of the already-poured paste. A top glass plate was then added over the covering sheet, and suitable weights were set on the glass plate so as to ensure even distribution of the paste between the two plastic sheets. The thickness of the dressing pad was controlled by the thickness of the shims. Two hours after pouring the synthetic resin wound dressing, the upper glass plate was removed and the pad was trimmed and shaped, the top and bottom sheets remaining in place on the pad. Then, one of the plastic sheets was gently peeled from the pad so as to expose one pad surface for evaluation (see Example 3). The formulations for Formulas X–XIV are presented below in Table III.

TABLE III

Formula #X:   4.46%   DMSO: 48.22%  PEG: 47.32%  PHEMA
Formula #XI:  0.0%    DMSO: 55.0%   PEG: 45.0%   PHEMA
Formula #XII: 5.0%    DMSO: 53.0%   PEG: 42.0%   PHEMA
Formula #XIII: 10.0%  DMSO: 55.0%   PEG: 35.0%   PHEMA
Formula #XIV: 15.0%   DMSO: 50.0%   PEG: 35.0%   PHEMA

EXAMPLE 4

This example, Formulations XII–XIV heretofore described in regard to Example 3 and five additional formulations (i.e., Formulas XV–XIX) were mixed and were poured into a heavy-duty aluminum cups. After set-up occurred (i.e., after the paste had acquired the appearance of an occlusive, non-sticky plastic pad), an aluminum foil cover sheet was placed over the pad and sealed to the aluminum cup via suitable plastic film adhesive tape. The cups were then placed within polyethylene storage bags and sealed for a substantial length of time (e.g., several days). More specifically, each of the aluminum foil cups had a diameter of 35 mm., a depth of 3.175 mm., a surface area of approximately 9.62 cm$^2$, and a volume of about 3 cc.

After the cups were removed from their polyethylene storage bags, the structural integrity and potential utility of each of the pads was rated according to its clarity (transparency), flexibility, adhesiveness, and rebound to its original shape after stretching. Formulations for the samples utilized in this example, together with comments on their rating as burn dressing, are presented in Table IV below.

TABLE IV

| Formulation # | DMSO % | PEG % | PHEMA % | Rating |
|---|---|---|---|---|
| XII | 5.0 | 53.0 | 42.0 | Good Flexibility (F), good Rebound (R), good Clarity (C), moderate Adherence (A) |
| XIII | 10.0 | 55.0 | 35.0 | Good F, R, C and A |
| XIV | 15.0 | 50.0 | 35.0 | Good F, R, C, excellent A |
| XV | 15.0 | 55.0 | 30.0 | Good F, R, C, excellent A |
| XVI | 20.0 | 45.0 | 35.0 | Good F, R, C, excellent A |
| XVII | 20.0 | 50.0 | 30.0 | Good F, R, C, excellent A |
| XVIII | 50.0 | 20.0 | 30.0 | Good F, C, excessive adherence, excessive fluidity |
| XIX | 50.0 | 30.0 | 20.0 | Excessive adherence, excessive fluidity |

EXAMPLE 5

Here, a preparation of synthetic resin wound dressing of the present invention containing an active cardiovascular medicament was prepared, wherein the medicament mixed with the paste was nitroglycerine, and wherein the nitroglycerine was present in a concentration of 10% by weight of the PEG solvent. The resin paste was mixed by adding PEG, with and without the presence of nitroglycerine, to a mixing dish containing the PHEMA polymer, The resulting paste was then mixed thoroughly for several minutes. Then, the DMSO plasticizer was added to the mixed paste and vigorously stirred for about 10–15 seconds. The mixed resin paste was then poured into preformed aluminum cups, similar to those described in Example 4. With the high concentration of DMSO utilized in this Formulation XX (e.g., 15% DMSO: 48% PEG: 35% PHEMA: and 2% nitroglycerine), set-up occurred rapidly after pouring of the mixed paste into the aluminum foil cups. After set-up of the resulting paste had occurred, aluminum foil cover sheets were applied to the open face of the paste, and these aluminum foil cover sheets remained in position until immediately prior to the application of the synthetic resin pad on the skin. The synthetic resin pad was permited to cure (e.g., overnight).

When the pad was to be applied to the skin, the top aluminum foil cover sheet was gently removed and the exposed pad surface was placed firmly onto the desired surface area of the skin. An adhesive overlay ring, or appropriate strips of adhesive tape or the like, was placed over the aluminum cup retaining the synthetic resin pad securing the exposed surface of the pad within the cup firmly on the surface of the skin. The adhesive covering kept the pad edges from becoming dislodged from the skin, and the inherent adhesiveness of the cured pad resulted in excellent continual skin contact and adherence for more than five days.

EXAMPLE 6

Here, three additional formulations (e.g., Formulas XXI–XXIII) were prepared of synthetic resin wound dressing of the present invention containing an active medicament in which the medicament agent was nitrofurazone (NF), an antimicrobial agent. This synthetic resin wound dressing incorporating the NF medicating agent was evaluated for specific antimicrobial activities against two selected microorganisms, *Psuedomonas aeruginosa* and *Staphylococcus aureus*, in a laboratory in-vitro test model. More specifically, this test model examined the penetration of the NF medicament agent from the medicated synthetic resin wound dressing of the present invention through a blood-soaked batiste gauze positioned between the medicated wound dressing of the present invention and a microbial innoculated agar surface.

The formulations utilized in this example are presented in Table VIA.

TABLE VIA

| | | | | |
|---|---|---|---|---|
| XXI 4.47% | DMSO: 50.08% | PEG: 45.22% | PHEMA: 0.2% | NF |
| XXII 4.7% | DMSO: 52% | PEG: 43.1% | PHEMA: 0.2% | NF |
| XXIII 4.7% | DMSO: 52% | PEG: 41.3% | PHEMA: 2.0% | NF |

In preparing the medicated synthetic wound dressings described by Formulations XXI–XXIII, as described in Table VIA, the nitrofurazone antimicrobial agent was placed into a mixture of the PEG solvent and DMSO plasticizer and mixed for approximately 2 minutes. Then, the PHEMA polymer was added and mixed for an additional 2 minutes. The resulting paste was then poured onto plastic film sheets approximately 4 inches × 4 inches (10.2 × 10.2 cm.), and a 1.0 mm. shim was placed around the edges of the base plastic sheet. A covering plastic film sheet was positioned over the pour, and a glass plate was placed over the sheet supported by the shims, and suitable weights were set on the glass plate so as to ensure that a pad of the medicated synthetic resin material of a desired uniform thickness (e.g., 1.0 mm.) was formed. The overlying glass plate was removed after about 2–4 hours and the medicated synthetic resin dressing sandwiched between the plastic cover sheets was trimmed to a desired size.

A comparative evaluation study was conducted to ascertain the microbial inhibition characteristics of the above-described medicated synthetic wound dressings. In this study, the medicated synthetic resin wound dressing was wrapped in batiste gauze, saturated with human whole blood, in such manner that a single layer of the treated gauze remained between the selected medicated dressing and an agar surface which had been innoculated with a predetermined number of *Psuedomonas aeruginosa* or with *Staphylococcus aureus*. After 24-hour contact periods, the medicated dressings were removed intact from the innoculated agar surfaces and placed on a new innoculated agar surface within a Petri dish. The zone of clearing or bacterial killing was measured as an estimate of effective drug release. The specimen was then reincubated and the new cleared zone size determined. This procedure was repeated until there was no further activity from the test sample, or for a maximum of 7 days. The zone sizes were determined in millimeters, and are an average of three separate test samples.

It was concluded that Formulation XXIII exhibited substantially no activity against *Pseudomonas aeruginosa*. However, this would be expected since nitrofurazone is known to be ineffective against this microorganism.

When the medicated synthetic resin incorporating a 2% nitrofurazone (i.e., Formulation XXIII) was evaluated against *Staphylococcus aureus*, the zones of antimicrobial activity were as followed in Table VIB, presented below.

TABLE VIB

| Day 1 | Day 2 | Day 3 | Day 4 | Day 5 | Day 6 | Day 7 |
|---|---|---|---|---|---|---|
| 8.8 mm | 5.9 | 9.3 | 7.2 | 7.3 | 3.9 | 4.8 |

In the comparison testing of Formulations XXI–XXIII, as presented in Table VIA, zone differences of greater than 2 mm. were considered as a significant indicator of antimicrobial activity. It was thus concluded that 7 transfers over 7 days with the medicated wound dressing of the present invention, including a 2% nitrofurazone (NF) antimicrobial agent, exhibited release of the active antimicrobial agent with the resultant significant bacterial effects against *Staphylococcus aureus* innoculated agar plates.

EXAMPLE 7

In this example, 5 additional formulations, as indicated by Formulas XXIV–XXVII in Table VII, were mixed in which another antimicrobial agent, silver sulfadiazine (AgSD) was incorporated into the synthetic resin wound dressing of the present invention, resulting in a preformed, medicated synthetic resin wound dressing of the present invention. Generally, these preformed medicated wound dressings were mixed in form in the same manner heretofore described in Example 6, between plastic film face sheets. However, the silver sulfadiazine antimicrobial agent was weighed out and mixed with a predetermined weight of the PHEMA polymer. Then, the PEG solvent and DMSO plasticizer were introduced and mixed for about 2 minutes.

TABLE VII

| FORMU-LATION NO. | DMSO % | PEG % | PHEMA % | AgSD % |
|---|---|---|---|---|
| XXIV | 4.62 | 49.67 | 40.64 | 5.08 |
| XXV | 4.24 | 45.67 | 44.82 | 5.27 |
| XXVI | 4.45 | 47.69 | 42.58 | 5.28 |
| XXVII | 4.65 | 50.3 | 44.83 | 2.27 |
| XXVIII | 4.17 | 50.0 | 41.67 | 4.17 |

EXAMPLE 8

In this set of tests, various synthetic resin wound dressing of the present invention containing an active medicament were tested in-vitro. The antimicrobial agent evaluated for time release was silver sulfadiazine, a component of Formulation XXVIII, as set forth in Table VII. Another formulation, Formulation XXIX consisting essentially of 4.35% DMSO; 52.17% PEG; and 43.48% PHEMA (by weight) was also used. Reference should be made to the heretofore discussed formulation of wound dressing in regard to Examples 3 and 6, with and without the presence of medicaments. Each of the preformed, cured synthetic resin wound dressings, in accordance with Formulations XXVIII and XXIX were prepared. The in vitro tests were performed on actively growing *Staphylococcus aureus* specimens freshly distributed on brain/heart infusion agar in standard Petri dishes. The test discs (i.e., 20×20 mm. squares of the test materials) were placed on the contaminated agar and the dishes were incubated in upright position so as to prevent the disc from falling off the agar surfaces. The discs and Petri dishes were incubated at 37° C. for 24 hours.

A well-defined area in which all of the bacteria were killed was measured around the discs. The diameter of the clear area outside the discs was then determined by subtracting the disc diameter from the diameter of the clear area. The diameter cleared was utilized as an estimate of the effectiveness of the antimicrobial activity, as well as an indicator of the release dynamics of the antibiotic agent (i.e., silver sulfadiazine) from the preformed medicated wound dressing of the present invention. The test discs contained either 4.17% by weight of silver sulfadiazine (Formulation XXVIII), or no silver sulfadiazine (Formulation XXIX). The discs were serially transferred each day for 4 days to new agar plates freshly seeded with *Pseudomonas aeruginosa* from actively growing cultures, and the new plates were placed into an incubator. The purpose of this in vitro test was to evaluate the potential long-term release of the active antimicrobial agent silver sulfadiazine from the synthetic resin wound dressing of the present invention containing an active medicament.

The results of the clearing tests indicating control of the bacterial proliferation are shown in Table VIII below.

TABLE VIII

| Day | XXVIII (AgSD) | XXIX |
|---|---|---|
| 1 | 25 mm | 0 mm |
| 2 | 13 | 0 |
| 3 | 12 | 0 |
| 4 | 11 | 0 |

It was concluded that the synthetic resin medicated wound dressing, made in accordance with Formulation XXVIII containing 4.17% of silver sulfadiazine (by weight), released sufficient levels of the active antimicrobial medication so as to kill the bacteria on the agar surface for as long as 4 days, whereas the synthetic resin dressing without the antimicrobial agent did not evidence any detected antibacterial effects.

EXAMPLE 9

A series of tests was initiated to determine the effective synthetic resin wound dressing of the present invention containing an active topical medicament in which the active agent was silver sulfadiazine on infected, burned rats. This study evaluted the survival rates of burned and *Pseudomonas aeruginosa* contaminated rats treated with synthetic resin wound dressing of the present invention in which the medicament was silver sulfadiazine. A synthetic resin wound dressing of the present invention, absent of preloaded antimicrobial medication, was used as a control. The unmedicated control wound dressing formulation was as described above in Example 8, and as previously identified as Formulation XXIX. The medicated synthetic wound dressing was also the same as described in Example 8 as formulaion XXVIII.

In conducting this test, 18 Sprague-Dawley strain rats were each injected with 10 cc of Lactate-Ringers (I.P.) and were scald burned (third degree) over a 2×3 inch (5×7.6 cm.) area of their backs. Each of the rats had an average weight prior to being burned of approximately 250 grams. The burned area of each rat was contaminated with 1 ml. of actively growing culture of *Pseudomonas aeruginosa* containing $10^6$ *Pseudomonas aeruginosa*. Within one hour after being burned the eschars were removed from the wounds and the wound dressings of this invention made in accordance with Formulations XXVIII and XXIX, heretofore described, were applied to cover the entire wound area with the outer plastic film face sheet remaining intact on the synthetic resin wound dressing. There were 9 rats in each treatment group (i.e., 9 of the 18 rats were treated with a medicated wound dressing made in accordance with Formulation XXVIII, and 9 of the rats were treated with an unmedicated wound dressing made in accordance with Formulation XXIX).

The results of this testing showed that within one to three weeks after the burn injury and the bacterial contamination, all of the animals treated with the unmedicated wound dressing made in accordance with Formulation XXIX were dead. In comparison, only one of the rats treated with the silver sulfadiazine medicated agent, in accordance with Formulation XXVIII had died, with 8 of the 9 surviving after 3 weeks. It was concluded that this test demonstrated the protective effect of the silver sulfadiazine medicated agent delivered by the synthetic resin wound dressing of the present invention. Further, it was concluded that no apparent interference resulted from the DMSO plasticizer on the activity of the medicated agent.

EXAMPLE 10

This study examined the relative effectiveness of the synthetic resin wound dressings of the present invention, with and without the presence of a preloaded medicament (e.g., silver sulfadiazine), on *Pseudomonas aeruginosa* counts taken from infected burn wounds 4 days after the dressings were applied to experimental, controlled infected burn wound sites. Also, body weights were determined for each group of experimental rats when they entered the study and on the eighth day after the specimen animals were burned. This interval was chosen to allow for the effects of the treatment and to allow later times when many of the control rats were dead.

The same experimental procedures as utilized in Example 9, heretofore described, were applied in the study of Example 10 in which adult Sprague-Dawley strain rats were burned by exposing 37.5 cm.$^2$ area of their backs to 95° C. water for 10 seconds. The rats were weighed and injected with a 10 cc. Ringer solution (I.P.). One cc of $10^6$ of *Pseudomonas aeruginosa* was disposed on the wound site. Synthetic resin wound dressings of the present invention, with and without silver sulfadiazine (the antimicrobial agent) were applied to the burn wound sites. The unmedicated wound dressings utilized in this study were made in accordance with Formulation XXX, which consisted essentially of 4.7% DMSO: 52.0% PEG: and 43.3% PHEMA, by weight. The medicated synthetic wound dressing was made in accordance with Formulation XXXI, which consisted essentially of 4.7% DMSO: 52.0% PEG: 41.3% PHEMA: and 2.0% silver sulfadiazine.

Figure 2:
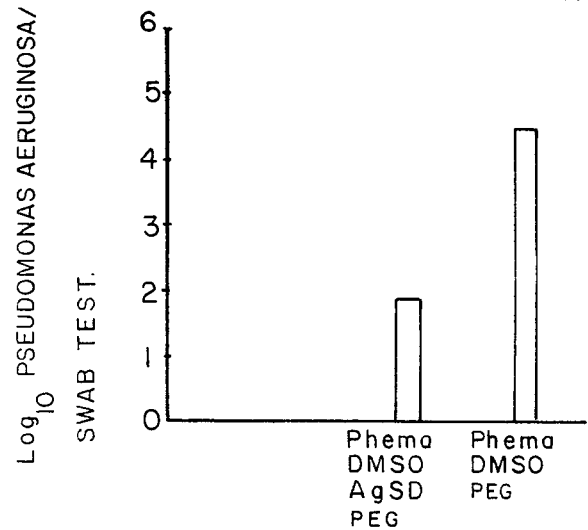
FIG. 2 is a graph of the antibacterial effectiveness of the wound dressing of the present invention in a rat burn contaminated model test.

Following the burning of the test animals, the bacterial counts and body weights of the test animals were evaluated. In FIG. 2 of the drawings, it can be seen that the PHEMA, DMSO, AgSD synthetic resin wound dressing of the present invention had a profound antibacterial effect on the Pseudomonas aeruginosa contaminated test animals reducing the wound contamination by more than a hundred fold compared to the wounds in the rats treated with the unmedicated dressing. A statistical analysis of this effect using the Student's t-Test yielded a probability of p less than 0.001.

Figure 3:
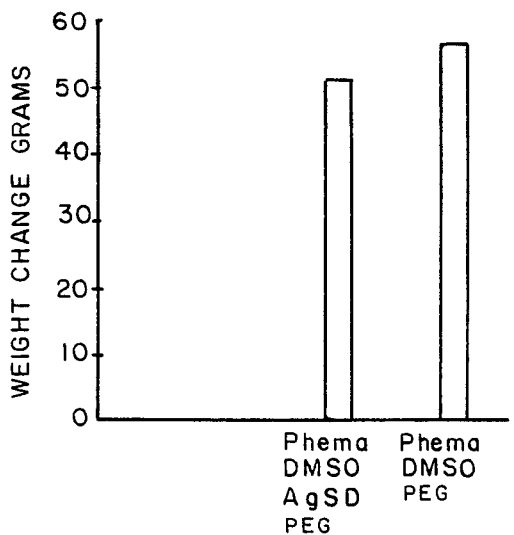
FIG. 3 is a graph of the loss of body weight (grams) by rats burned in the burn test of FIG. 2 when treated with the dressing of the present invention.

As shown in FIG. 3, while the burned test animals treated with the silver sulfadiazine medicated wound dressing of the present invention underwent a similar weight loss compared to the burned animals treated with the unmedicated synthetic resin wound dressing of the present invention. It was found that no statistically significant differences were observed on the decrease in body weight.

EXAMPLE 11

A series of test was conducted utilizing medicated synthetic wound dressing of the present invention containing a 2% silver sulfadiazine antimicrobial agent, with the synthetic resin wound dressing applied to a bidirectionally elastic substrate, generally as illustrated in FIG. 1. More specifically, the medicated synthetic wound dressing was formulated in accordance with Formulation XXXI, described in Example 10, with the exception that the paste, prior to curing, was applied to the substrate. The substrate 3 shown in FIG. 1, as utilized in the wound dressings in Example 11, was an International Paper-758 burn dressing having a nylon surface onto which the synthetic resin would dressing paste was poured, and having an outer or downwardly facing silicone face. After the wound dressing paste was poured onto the substrate, a cellophane backing sheet 7 was placed over the paste and 1.0 mm. metal shims were positioned adjacent the bandage so as to regulate the thickness of the paste on the substrate. Then, weights were applied to the top glass plate regulating the formation of a uniform coating thickness of the synthetic resin wound dressing.

It will be appreciated that substrate 3, as illustrated in FIG. 1, due to its elastic properties, provides a support system for the medicated synthetic resin wound dressing, thus limiting stretching and bending of the preformed, fully cured synthetic resin wound dressing pad and diminishing the chances of tearing or cracking of the pad which would, of course, result in a loss of the antimicrobial barrier effect of the pad. Additionally, the outer silicone surface of substrate 3 permitted subsequent wrapping of the medicated wound dressing after its application to a wound with a gauze cover in such manner that the gauze would not adhere to the medicated dressing and dislodge the medicated dressing from the wound site when or if it was necessary to remove the gauze cover. Continuous application of the synthetic resin wound dressing is advantageous since it reduces the likelihood of environmental contamination of the injured area.

EXAMPLE 12

In this example, a variety of formulations, as set forth in Table XII below, of both medicated nd non-medicated synthetic resin wound dressings of the present invention, were mounted on a nylon, elastic fabric which was stretchable in both widthwise and lengthwise directions. More particularly, the substrate was a nylon/Lycra fabric commercially available from Tweave, Inc.

TABLE XII

| XXII | 5% DMSO: 53% | PEG: 42% | PHEMA 0% AgSD |
|---|---|---|---|
| XXXII | 5% DMSO: 53% | PEG: 40% | PHEMA 2% AgSD |
| XXXIII | 5% DMSO: 53% | PEG: 41% | PHEMA 1% AgSD |
| XXXIV | 5% DMSO: 60% | PEG: 35% | PHEMA 0% AgSD |
| XXXV | 5% DMSO: 60% | PEG: 33% | PHEMA 2% AgSD |
| XXXVI | 5% DMSO: 58% | PEG: 35% | PHEMA 2% AgSD |
| XXXVII | 5% DMSO: 55% | PEG: 35% | PHEMA 5% AgSD |
| XXXVIII | 5% DMSO: 55% | PEG: 38% | PHEMA 2% AgSD |
| XXXIX | 5% DMSO: 58% | PEG: 37% | PHEMA 0% AgSD |
| XXXX | 5% DMSO: 57% | PEG: 36% | PHEMA 2% AgSD |
| XXXXI | 5% DMSO: 58% | PEG: 36% | PHEMA 1% AgSD |
| XXXXII | 5% DMSO: 59% | PEG: 36% | PHEMA 0% AgSD |
| XXXXIII | 5% DMSO: 56% | PEG: 34% | PHEMA 5% AgSD |

In formulating the above preparations, the PEG solvent was added to the preweighed PHEMA polymer and AgSD. The mixture was stirred vigorously for several minutes. The DMSO plasticizer was then added, and mixing continued for several additional minutes. After 5 minutes, the resulting slurry or paste was poured onto plastic film sheets resting on a glass plate. Then 0.5 mm. shims were placed along the edges of the plastic film and a trowel was used as a screed bearing on the shims so as to spread the paste over the bottom plastic film forming a pad having a substantially uniform thickness of about 0.5 mm. After about 10–20 minutes, the gel set-up (i.e., a non-tacky film was formed on the pad), and then the above-mentioned nylon/Lycra substrate was placed on top of the gelled pad. A top glass plate was applied to the substrate, with the substrate and the top glass plate bearing on the shims. Weights were added to the resulting stack and it was cured in this stacked arrangement overnight (or for a minimum of 4 hours after pouring). After curing, the weights, glass plates, and shims were removed, and the medicated wound dressing comprising the fabric substrate, the gelled synthetic resin wound dressing pad, and the plastic film cover or backing sheet were trimmed to a desired size and placed into polyethylene coated, aluminum foil envelopes, and sealed to await use. From a small number of samples prepared as long as 12 months prior to evaluation, it was observed that the adherence and flexibility characteristics of the medicated dressing were retained and active drug release was demonstrable.

EXAMPLE 13

In these experiments, in vitro antibacterial assessments were conducted with 0.5 mm. and 1.0 mm. thicknesses of medicated synthetic resin wound dressings containing 1 and 2% silver sulfadiazine (AgSD) medicaments. Basically, the medicated wound pad dressings were formulated in accordance with Formulations XXXX and XXXXI, as set forth in Table XII above. These formulations were prepared in the manner described in regard to Example 12, except for the preparation of the 1.0 mm. thick medicated dressing pads, a 1.0 mm. shim was utilized. Evaluation of the antibacterial activity was made utilizing 0.5 inch (1.2 cm.) diameter discs.

Generally, the experimental procedures utilized in this antibacterial activity evaluation were the same as heretofore described in Example 8. The results of this testing is shown in Table XIII below.

TABLE XIII

| Day of Transfer | Millimeters of Clearing Around Disc | | | |
|---|---|---|---|---|
| | Dressing plus AgSD (1%) Pad Thickness | | Dressing plus AgSD (2%) Pad Thickness | |
| | 0.5 mm | 1.0 mm | 0.5 mm | 1.0 mm |
| 1 | 20.75 | 22.25 | 22.25 | 17.0 |
| 2 | 18.25 | 19.25 | 20.0 | 17.75 |
| 3 | 18.25 | 17.75 | 18.0 | 21.25 |
| 4 | 15.0 | 17.5 | 16.5 | 16.0 |
| 5 | 17.0 | 18.0 | 26.25 | 21.5 |
| 6 | 16.0 | 16.5 | 16.5 | 16.0 |
| 7 | 16.75 | 16.0 | 27.25 | 17.0 |
| 8 | — | 16.0 | 17.0 | 18.0 |
| 9 | — | 19.25 | 19.25 | — |
| 10 | | 15.0 | 15.0 | |
| 11 | | — | 13.5 | |
| 12 | | — | | |

In general, there appeared to be a relationship between the thickness of the medicated wound dressing pad, the concentration of the antimicrobial agent (e.g., silver sulfadiazine), and the bactericidal effects such that higher concentrations of the antimicrobial agent exhibited longer durations of the antimicrobial actions of the medicated wound dressing.

EXAMPLE 14

An in vitro assessment was performed on the antibacterial activity of the synthetic resin wound dressing of the present invention without an antimicrobial agent. This was compared with the wound dressings of the present invention, containing predetermined amounts of the antimicrobial agent silver sulfadiazine (AgSD) (i.e., 1.0%, 2.0%, and 5.0% by weight). Formulations for the nonmedicated and medicated wound dressings are shown below in Table XIV.

TABLE XIV

| XXXXII | 5% DMSO: 59% | PEG: 36% | PHEMA 0% AgSD |
| XXXXI | 5% DMSO: 58% | PEG: 36% | PHEMA: 1% AgSD |
| XXXVI | 5% DMSO: 58% | PEG: 35% | PHEMA: 2% AgSD |
| XXXIII | 5% DMSO: 56% | PEG: 34% | PHEMA: 5% AgSD |

The medicated and nonmedicated synthetic resin wound dressings had a pad thickness of either about 0.5 or 1.0 mm., and were prepared according to the procedures heretofore described in regard to Example 12. The in vitro antimicrobial evaluation testing and methodology was essentially identical to that as described in regard to Example 8.

The results summarized in Table XIV A, for the thin (0.5 mm.) discs show a progressive increase in effective days as the drug concentration increases from 0% to 5% of the dressing weight. Days of the clearing of greater than 2 mm. beyond the edge of the test disc were 0, 4, 6.5, and 9, as the AgSD was varied 0%, 1%, 2%, and 5%, respectively. The 1.0 mm. dressing with 1% AgSD showed activity with Δ̄ clearing of 2 mm. for 7 days which was almost twice the 0.5 mm. tests with the 1% AgSD and similar to the 6.5 day with the 2% AgSD in the 0.5 mm. test discs. The 1 mm. discs with 2% AgSD did not appear to produce the expected length of activity relative to the thin discs with 2% AgSD. The test with 2% AgSD was repeated with similar results. It appears likely that once the concentration of silver sulfide dioxene is 2% or more, the release of the anti-microbiol is independent of the thickness of the dressing.

TABLE XIV A

IN VITRO STUDY OF ANTIMICROBIAL ACTIVITY OF DIMAC/PLUS (Δmm. CLEARED)

| % AgSD | 0 | 1 | 1 | ·2 | 2 | 2 | 2 | 5 |
|---|---|---|---|---|---|---|---|---|
| thickness | 0.5 | 0.5 | 1.0 | 0.5 | 0.5 | 1.0 | 1.0 | 0.5 |
| days-test | | | | mm. | | | | |
| 1 | 1.7 | 8.8 | 7.0 | 9.0 | 8.5 | 5.8 | 11.0 | 8.5 |
| 2 | 0.5 | 7.5 | 8.8 | 8.5 | 7.0 | 3.5 | 7.5 | 7.3 |
| 3 | 0.5 | 3.3 | 6.0 | 5.8 | 6.5 | 2.0 | 5.3 | 9.3 |
| 4 | 0 | 2.0* | 3.8 | 4.5 | 5.0 | 2.3 | 4.0 | 8.2 |
| 5 | | 1.8 | 3.3 | 4.8 | 4.5 | 2.0 | 3.8 | 6.3 |
| 6 | | 0 | 3.0 | 3.2 | 2.5 | 1.0 | 2.5 | 4.3 |
| 7 | | | 2.8 | 2.8 | 0 | 1.0 | 0 | 5.0 |
| 8 | | | 1.5 | 1.5 | | 1.0 | | 3.0 |
| 9 | | | 1.5 | 1.3 | | 0 | | 2.5 |
| 10 | | | 1.0 | 1.3 | | | | 1.8 |
| 11 | | | 0 | 0 | | | | 0 |

*Underlined values = last day of transfer with Δ greater than 2 mm. clearing.

EXAMPLE 15

The therapeutic effects of synthetic resin wound dressing of the present invention having varying amounts of silver sulfadiazine (AgSD) antimicrobial agent therein was tested against the survival and bacterial contamination of burn wounds induced in rats. The formulations for the wound dressings utilized in this study were identical to Formulations XXXXI–XXXXIV, as described in Table XIV above. The pads were prepared to have a relatively uniform pad thickness of approximately 0.5 mm., and the synthetic resin wound dressings were prepared in accordance with the methodology and procedures heretofore described in Example 12.

A modification of the survival study protocol, as heretofore described in regard to Example 9, was utilized to allow for assessment of the degree of antimicrobial activity exhibited by different formulations of the invention. Specifically, in this study, 75 rats were scald-burned, utilizing 95° C. water for 10 seconds on a 23 cm.$^2$ (3.5 cm.×6.5 cm.) area on their backs and the eschar was removed. Then, the escharectomized wounds were contaminated within one hour of the burn injury with 1 ml of a microbial medium containing $10^6$ Pseudomonas aeruginosa. The test animals were then segregated into 5 treatment groups of 15 animals each and observed for 20 days. Four of the treatment groups of animals had the synthetic wound dressings of the present invention applied to their wound sites, with the various wound dressings containing 0%, 1.0%, 2.0%, or 5.0% silver sulfadiazine (AgSD), according to the formulations set forth above in Table XIV. The fifth treatment group of test animals received daily treatment with SILVADENE cream, commercially available from Marion Laboratories, Inc., of Kansas City, Mo., containing 1% silver sulfadiazine. Test groups being treated with the wound dressings of the present invention were changed every 4 days so that each test animal received 5 dressings, while the test group receiving the SILVADENE cream, treated by applying the SILVADENE cream each day for the 20-day post-burn observation period. At the 4-day dressing changes, the wounds were evaluated using a wet swab rolled over the wound to collect and estimate their bacterial content. The bacteria on the swabs were extracted in a 10 ml quantity of saline solution. The suspension of bacteria were serially diluted, and aliquots distributed on agar plates. The bacterial counts on the agar plates permitted an estimate ($\log_{10}$/swab) of the bacterial contamination on the burn wound sites. Daily survival observations were recorded throughout the 20-day observation periods and body weights were also recorded during the experimental periods.

Seven percent of the rats treated with DIMAC (without AgSD) survived the 20-day period of observation (Table XVA). The groups treated with 1%, 2%, and 5% AgSD in DIMAC/Plus (i.e., DIMAC plus a medicament) showed 93%, 100%, and 93% survival. Treatment with SILVADENE produced a 73% survival in that test group.

TABLE XVA
PERCENT SURVIVAL OF BURNED AND INFECTED RATS TREATED WITH DIMAC/PLUS OR SILVADENE

| DIMAC/PLUS % AgSD | | | | |
|---|---|---|---|---|
| 0 | 1 | 2 | 5 | SILVADENE |
| 7 | 93 | 100 | 93 | 73 |

The mean time to death with an assumed 20-day maximum survival period was examined. The DIMAC/Plus group without AgSD had an 8-day average. All the other test groups were clustered above 17 days. This reflects the extended survival and few deaths in the rats treated with either DIMAC/Plus AgSD or SILVADENE.

Figure 8:
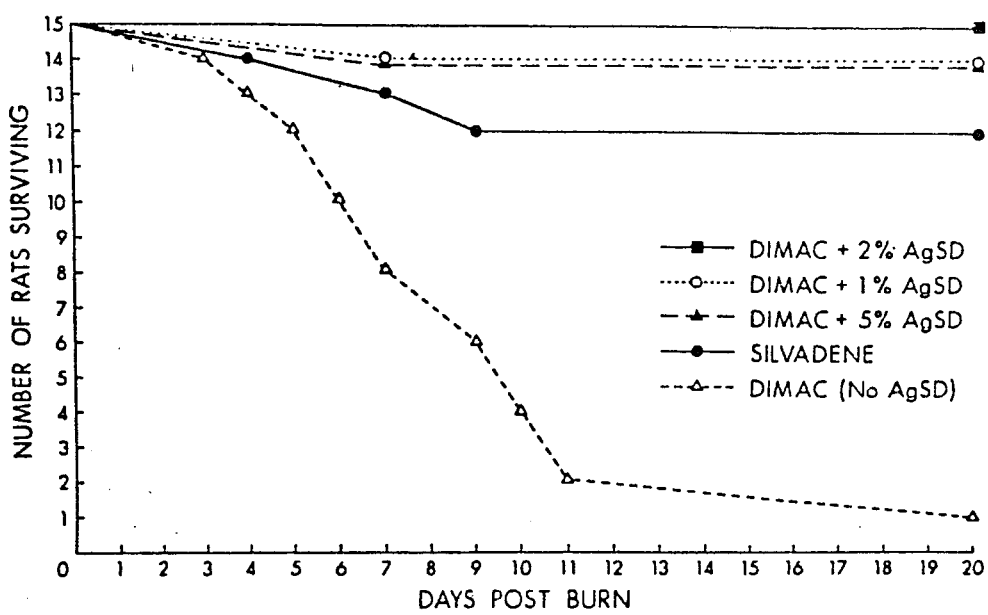
FIG. 8 is a plot of the survival of burned rats treated in accordance with Example 16.

FIG. 8 shows survival curves for the five test groups during the 20-day observation period. Only the DIMAC (i.e., no AgSD) panel show a substantial number of deaths; 13 of the 14 deaths occurred during the first 11 days of the test.

Scar healing in a representative rat from each treatment group was observed, and all healed to form a linear scar, except the one surviving rat in the DIMAC-treated group, whose wound was not contracted by the 20th post-burn day.

Table XV B reports the mean log swab counts for wound bacterial cultures of *Pseudomonas aeruginosa* in the burned and contaminated rats. These swabs were obtained 4 days following the burn injury and wound contamination with *Pseudomonas aeruginosa*. The rats whose wounds were covered with DIMAC/Plus (without AgSD) had a mean log count of 6.8 *Pseudomonas aeruginosa* $\pm$ a standard error (S.E.) of 0.39. With the DIMAC/Plus containing 1% AgSD, the mean log count was 4.5 *Pseudomonas aeruginosa*. The addition of 2% AgSD to the DIMAC/Plus reduced the count to 3.5 and with 5% AgSD in DIMAC/Plus the mean log swab count was 3.0 with an S.E. of 0.4. All the dressings were continuously in place for 4 days. The rats treated daily with SILVADENE had a mean log count of 3.7±0.37 *Pseudomonas aeruginosa*. The 2% and 5% DIMAC/Plus dressings and the SILVADENE-treated group had bacterial counts which were 1000-fold less than those in the panel of rats treated with DIMAC (without AgSD). Statistical analysis of the data revealed no significant differences in the mean values obtained from the burn/contaminated wounds treated with either DIMAC/Plus 2% or 5% AgSD or SILVADENE. When the analysis of variance procedure included the values from the group treated with DIMAC/Plus 1% AgSD, a significant difference (p=0.039) in treatment effect was obtained.

TABLE XVB
WOUND CONTAMINATION DETERMINED BY THE WET SWAB TEST ON DAY 4 POST-BURN
(Mean $\log_{10}$ Swab Count for *Pseudomonas aeruginosa*)

| Test Group | % AgSD | # of Rats | Mean Log Ps.a. | Standard Error |
|---|---|---|---|---|
| DIMAC/Plus | 0 | 13 | 6.8 | 0.39 |
| | 1 | 15 | 4.5 | 0.36 |
| | 2 | 15 | 3.5 | 0.35 |
| | 5 | 15 | 3.0 | 0.40 |
| SILVADENE | 1 | 15 | 3.7 | 0.37 |

The rats were weighed prior to starting the tests and at the end of the test at 20 days. The results of these measurements are reported in Table XVC. The data on DIMAC (without AgSD) is not included in this Table because 14 of the 15 rats in this group died before the end of the observation period of 20 days.

TABLE XVC
WEIGHT CHANGES IN BURNED AND *PSUEDOMONAS AERUGINOSA* CONTAMINATED RATS TREATED WITH DIMAC/PLUS OR SILVADENE (15 rats/group)

| Treatment | % AgSD | Mean Weights Day 0 | Day 20 | Weight gms |
|---|---|---|---|---|
| DIMAC/Plus | 1 | 264 | 303 | 39 |
| | 2 | 270 | 316 | 46 |
| | 5 | 268 | 301 | 33 |
| SILVADENE | 1 | 269 | 272 | 3 |

All the rats treated with DIMAC/Plus AgSD demonstrated a means weight gain of 33 to 46 gm during the 20-day observation period. Rats whose wounds were covered with SILVADENE showed only a 3 gm increase in their mean weights.

The in vitro tests of the DIMAC/Plus dressings loaded with AgSD show an extended period of delivery of the active drug which is related to thickness of the preparation and to the concentrations of the AgSD. The 1.0 mm. dressing with 1% AgSD killed bacteria for 7 days, compared to 4 days for the 0.5 mm. preparation. Only the 1.0 mm. dressing with 2% AgSD failed to produce a clearance greater than the 0.5 mm DIMAC/Plus dressing loaded with 2% AgSD. The test was repeated and still failed to show any differences between the two preparations. Apparently, when the AgSD is 2% of the weight of the dressing, the time of drug release is independent of thickness. However, the demonstrated release of AgSD beyond 6 days by the 0.5 mm. dressing containing 2% of AgSD encouraged the further exploration of the 1%, 2%, and 5% preparations in a burned rat model.

Only 7% of the 15 rats whose infected burn wounds were covered with DIMAC alone survived the 20-day observation period. Most of the rats in this group died within the first 10 days of the 20-day test interval. Forty-three of the 45 rats treated with 1%, 2%, or 5% AgSD-loaded DIMAC/Plus dressing survived to the end of the predetermined observation period (FIG. 8). Three of the rats treated with SILVADENE died during the first 9 days of the test. These losses may be attributed to the daily manipulations necessary to change the dressings and to the irritation of removing the adhesive tape needed to hold the gauze in place.

The changes in weight during the test reflect the considerations mentioned above. The rats treated with DIMAC/Plus gained an average of about 1.5 gm/day while the SILVADENE group added only 0.1 gm/day.

The stress of the daily dressing changes may account for the minimal weight gain in the SILVADENE panel. The limited disturbance of the test subjects obtained by application of the DIMAC/Plus dressings with their extended period of drug release has potential benefits for clinical appliction.

Control of bacterial proliferation in the model burn wound was achieved with the DIMAC/Plus dressing containing 2% or 5% AgSD. The inhibition of burn wound bacterial contaminants with these two preparations appears equivalent to that obtained with SILVADENE. However, the DIMAC/Plus AgSD medicated dressings were only changed every four days, while the group receiving SILVADENE had daily dressing changes. The DIMAC/Plus 1% AgSD is not quite as effective as the dressings with higher AgSD content. Application of DIMAC with no added AgSD results in very high levels of wound bacteria and eventual death of the burned rats.

EXAMPLE 16

In this study, an examination of the changes induced by the inclusion of dimethylsulfoxide (DMSO) plasticizer on certain of the physical and functional characteristics of the synthetic resin wound dressing system of the present invention were evaluated. Specifically, medicated synthetic resin wound dressings of the present invention did undergo a variety of stress and elongation measurement. The investigations evaluate the modulus $f^*$, which is defined as the ratio of stress to strain, the maximum extensibility $\alpha_{-r}$, and the ultimate strength of the dressing, $f^*_r$. It was also an object of this study to examine the adhesive characteristics of the wound dressings of the present invention.

Generally, the previously identified Formulations XI, XII, XIII, and XIV were utilized together with Formulation XXXXIV with no DMSO. These formulations are presented below in Table XVI.

TABLE XVI

| Formulation XI 0% | DMSO: 55% | PEG: 45% | PHEMA |
| Formulation XII 5% | DMSO: 53% | PEG: 42% | PHEMA |
| Formulation XIII 10% | DMSO: 55% | PEG: 35% | PHEMA |
| Formulation XIV 15% | DMSO: 50% | PEG: 35% | PHEMA |
| Formulation XXXXIV 0% | DMSO: 55% | PEG: 35% | PHEMA: 10% H$_2$O |

The procedures employed for the preparation of the synthetic resin pads containing the various concentrations of DMSO and water utilized in this test are essentially as described in regard to Example 3. For Formulation XXXXIV, the procedure of preparation is identical to that used in regard to the preparation of Formulation XIII, except that 10% water, by weight, is substituted for the 10% DMSO by weight.

In making stress-elongation measurements, a strip of synthetic resin wound dressing was mounted between two clamps, with the lower clamp fixed and the upper clamp attached to a movable force gauge. A recorder was used to monitor the output of the force gauge as a function of time in order to obtain equilibrium values for the force suitable for comparisons. The sample was protected in an inert atmosphere (e.g., nitrogen) so as to prevent degredation of elastomeric network within the sample. A traveling microscope was utilized to obtain values of the strain by measuring the distance between two lines marked on the central portion of the test sample. The methodology utilized in this testing is more specifically set forth in "Rubber Elasticity", J. E. Mark, *Journal of Chemical Education*, Vol. 58, p. 898, November, 1981.

The nominal or engineering stress carried by the specimen is given by $f/A^*$, where f is the elastic force and where $A^*$ is the undeformed cross sectional area of the elastomeric test sample. Elongation was given by $\alpha = L/L_i$, where L and $L_i$ are the deformed and undeformed lengths of the sample, respectively.

One form of adhesiveness of the test samples was estimated by pressing each test sample against a 0.5 cm.×0.5 cm square area on the bottom of a clean glass slide, and by attaching a fixed weight to the opposite end of the test strip. The test thus involved peeling the strip away from the glass surface at an angle of approximately 90°.

Figure 4:
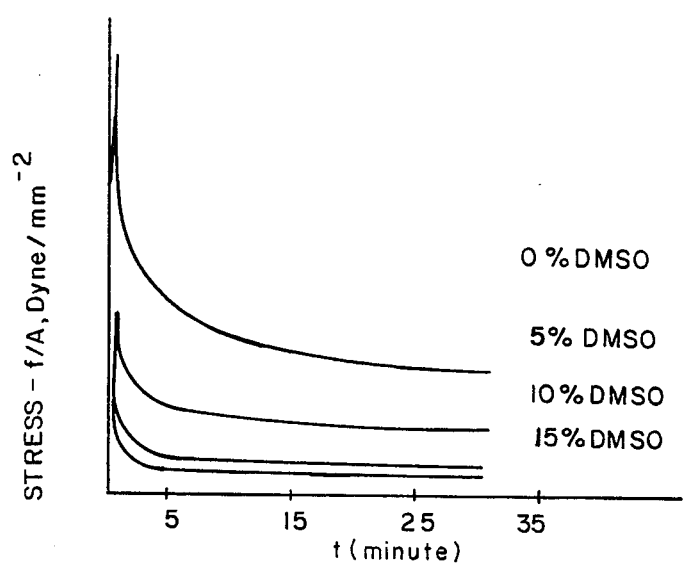
FIG. 4 is a plot of stress relaxation curves for a variety of formulations of the wound dressing of the present invention.

Referring to FIG. 4, the nominal stress, $f/A^*$, expressed in Dyne/mm$^2$, is illustrated. As shown in FIG. 4, each of the test specimens appear to have considerable relaxation in that the stress would drop off appreciably after initial loading, but, after about 5 minutes, a substantially constant stress level could be maintained. As is indicated in FIG. 4, the synthetic resin wound dressing having the highest load carrying capability contained no DMSO, and FIG. 4 further shows that there is a marked drop-off in ultimate stress which is proportional to the amount of DMSO. However, it has been found, even with high DMSO loadings, the stress carrying capabilities of the synthetic wound dressing of this invention are adequate, even when the wound dressing is applied as a paste in situ directly on the skin. Of course, if the synthetic resin wound dressing is carried by a fabric substrate, the stress carrying capability of the substrate has more than adequate strength to retain its initial structure when applied as a wound dressing.

Figure 5:
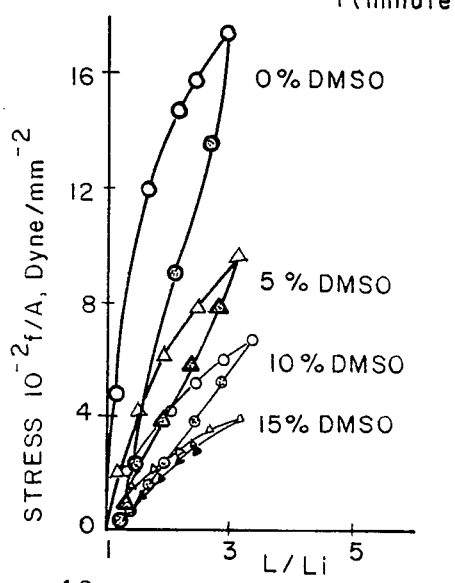
FIG. 5 is a plot of stress versus strain for a variety of formulations of wound dressings of the present invention.

Further, stress-relaxation tests conducted on the samples where the stress was plotted as a function of the ratio of deformed and undeformed lengths of the test specimens. The results of this testing is illustrated in FIG. 5 in which four families of curves are shown, the amount of DMSO contained in each of the specimens being as indicated on FIG. 5. The open data points indicate elongation data whereas the solid data points present the retraction phase of the elongation/relaxation cycle.

As can be seen in FIG. 5, the modulus of elasticity of the four samples differs considerably with the sample having no DMSO therein having the largest modulus of elasticity and thus being the hardest to deform, whereas the 15% by weight DMSO sample had the lowest modulus of elasticity and thus was easiest to deform. The samples also differed considerably in their respective amounts of hysteresis.

Figure 6:
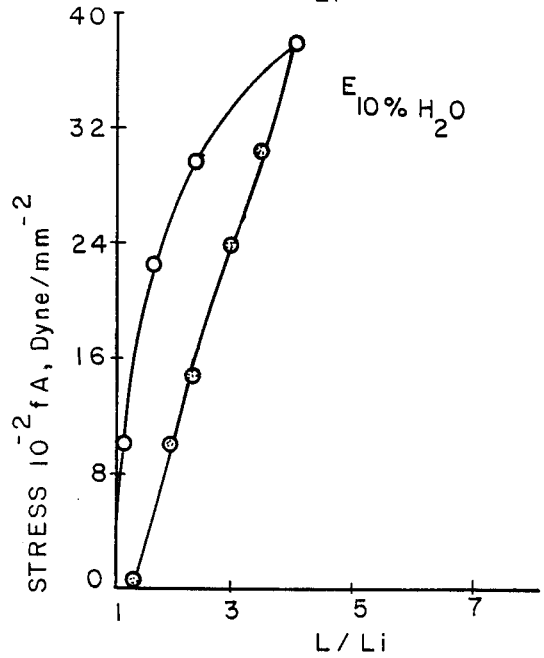
FIG. 6 is a plot of the stress strain curve for the modulus of elasticity of a wound dressing of the present invention with no DMSO included.

A similar stress, relaxation test was conducted on sample containing 0% DMSO, but having 10% water by weight. Results of this test are depicted in FIG. 6. This example had the largest modulus.

Additionally, tests were conducted to determine the maximum extensibility and ultimate strength of the various synthetic wound dressings made in accordance with the above-mentioned formulations, and the values of three different tests (and the averages thereof) of the various test samples are presented on Table XVIA below.

TABLE XVIA

Values of the Maximum Extensibility and Ultimate Strength

| Sample/Test | $\alpha_r$ | | | | $10^{2}/*_r$, N mm$^{-2}$ | | | |
|---|---|---|---|---|---|---|---|---|
| Wt % DMSO | 1 | 2 | 3 | Avg. | 1 | 2 | 3 | Avg. |
| 15 | 8.67 | 6.28 | 6.89 | 7.28 | 7.70 | 7.69 | 8.44 | 7.94 |
| 5 | 9.20 | 9.81 | 8.67 | 9.23 | 8.25 | 7.46 | 7.50 | 7.73 |
| 0 | 13.8 | 16.2 | 13.2 | 14.4 | 3.07 | 2.98 | 2.67 | 2.90 |
| 10 | 11.3 | 10.4 | 9.98 | 10.5 | 4.39 | 5.97 | 6.43 | 5.59 |
| 10 wt % H$_2$O | 8.50 | 8.45 | 7.90 | 8.28 | 12.5 | 11.1 | 10.5 | 11.4 |

Additionally, adhesion tests were performed on the various samples using the methodology heretofore described. In Table XVIB, the adhesion results using a 4.970 gm weight are tabulated, whereas in Table XVIC, the adhesion results using a 14.970 gm weight are tabulated.

TABLE XVIB

Adhesion Results, 4.970 g Weight

| Sample Wt % DMSO | Peel-Off Times* | | | | Observed Deformation Ratio |
|---|---|---|---|---|---|
| | 1 | 2 | 3 | 4 | |
| 0 | 10 days | — | — | — | 2.4 |
| 5 | 8 days | — | — | — | 4.0 |
| 15 | 2'29" | 2'48" | 3'18" | 4'50" | 8.0 |
| 10 | 12'10" | 7'55" | 8'20" | 6'30" | 5.6 |

*'-minutes, "-seconds

TABLE XVIC

Adhesion Results, 14.970 g Weight

| Sample Wt % DMSO | Peel-Off Times (Min.) | | | Observed Deformation Ratio |
|---|---|---|---|---|
| | 1 | 2 | 3 | |
| 0 | 13' | 20' | 15' | 8.0 |
| 5 | 75' | 65' | 78' | 5.0 |
| (10% H$_2$O) | 100' | 95' | 130' | 4.0 |

Still further, in this testing, the preferred polymeric system for the synthetic resin wound dressing of the present invention has heretofore been stated as consisting essentially of a mixture of polyethylene glycol (PEG) having a molecular weight preferably ranging between about 400 and 800, poly(2-hydroxyethylmethacrylate), referred to as PHEMA, and dimethylsulfoxide, referred to as DMSO. Other polymers, which although may not be as preferable as the above-mentioned PEG solvent, PHEMA polymers, and DMSO, might be useful as a replacement or as a substitute. In particular, other such replacement polymers or solvents could be poly(propylene glycol), poly(tetramethylene oxide), poly(1,3-dioxolane), poly(vinyl alcohol), and poly(caprolactam). Additionally, higher molecular weight PEG, up to about 2,000, may be used.

Additionally, other hydrogen bonding plasticizing agents, other than dimethylsulfoxide (DMSO) were investigated. DMSO was determined to have a solubility parameter, δ of 12. DMSO is moderately hydrogen bonding and has a solubility perameter of approximately 12 (cal/cm$^3$)$^{\frac{1}{2}}$. Therefore, other plasticizers known to be moderately hydrogen bonding and having solubility parameter near 12 (e.g., 10.7–12.6) should behave similarly to DMSO. Other hydrogen binding plasticizer solvents which might behave similarly, as judged by their hydrogen binding characteristics and solubility parameters, are given below in Table XVID.

TABLE XVID

Some Solvents Similar to DMSO

| Solvent | δ |
|---|---|
| Dimethyl phthalate | 10.7 |
| 2,3-Butylene carbonate | 12.1 |
| Dimethyl formamide | 12.1 |
| Dimethyl tetramethylene sulfone | 12.1 |
| Diethyl sulfone | 12.4 |
| Methylene glycolate | 12.4 |
| Methyl propyl sulfone | 12.5 |
| Butylrolactone | 12.6 |

EXAMPLE 17

In this study, the set-up times and physical characteristics of another formulation of other synthetic resin wound dressing formulations utilizing a different hydrogen bonding plasticizer in place of DMSO were investigated. Specifically, differing concentrations of N,N-dimethylformamide (DMFA) were used in place of DMSO. The formulations tested in this study are set forth in Table XVIIA below:

TABLE XVIIA

Formulations:

| XXXXV | 5% DMFA: | 53% PEG: | 42% PHEMA |
| XXXXVI | 10% DMFA: | 55% PEG: | 35% PHEMA |
| XXXXVII | 15% DMFA: | 50% PEG: | 35% PHEMA |

Generally, these formulations utilizing DMFA were prepared by adding the PEG solvent to a container of the PHEMA polymer and by briskly mixing the ingredients for approximately 3 minutes. Then the specified DMFA concentrations (based upon a weight percentage of the final mixture) were added and the resulting formulation was mixed for an additional one minute. At this time, the resulting resin were poured onto a plastic film backing sheet. Set-up was again defined as the appearance of an occlusive, non-tacky pad, and the time at which an adhesive surface reappeared was also determined. The results of these formulations are set forth below in Table XVIIB, where all times reported are in minutes.

TABLE XVIIB

| Formulation | Set-Up Time | Sticky Time |
|---|---|---|
| XXXXV | 15–20 | 90 |
| XXXXVI | 10–13 | 40 |
| XXXXVII | 4–7 | 25 |

The solvent DMFA is moderately hydrogen bonding and has a solubility parameter generally similar to DMSO. It was concluded that the addition of DMFA to the PEG/PHEMA polymer system in increasing concentrations shortened the set-up time of the resulting synthetic resin paste, and also decreased the time for appearance of an adhesive surface to develop on the gelled polymer system. Thus, the addition of a hydrogen bonding agent appears to be responsible for the enhanced set-up times observed and for other described changes in the physical and functional characteristics similar to the changes reported in the previous examples upon the addition of DMSO hydrogen bonding plasticizer. While it is felt at this time that DMSO is the preferred hydrogen binding agent, other similar hydrogen binding agents, such as set forth in Table XVID, may be utilized in place of DMSO.

In summary, there has been a long-standing clinical need for a medicated wound dressing which has the characteristic of providing extending duration topical therapy with minimal side effects or risk. This need is most clear in the treatment of severe burn wounds that are likely to be or to become infected. Present state-of-the-art therapeutic procedures employ once or twice-a-day changes of medicated cream dressings. This procedure can be painful, time-consuming to the professional staff, expensive, and results in the periodic removal of an artificial barrier against nosocomial infections, even if the bandages are removed only for a short period.

Further, the medicated wound dressings, the concept, the formulations, and the laboratory findings, as presented herein, reveal that the medicated wound dressings of the present invention provide extended duration release of therapeutically effective concentrations of established antimicrobial agents over as many as 14 days. Additionally, the synthetic resin wound dressing system also serves well as an antimicrobial barrier over the burn wound site. Therefore, the application of a medicated wound dressing of the present invention obviates the need for periodic and frequent bandage changes, markedly reduces the cost of effective treatment, and saves considerable time for the treatment professionals, as well as for the patient. Still further, by varying the amount of the hydrogen binding plasticizer added to the polymer system, the set-up time of the synthetic resin wound dressing of the present invention may be preselected so as to allow sufficient time to permit the clinician to apply an in situ wound dressing directly on the wound site, and also to obviate the need for the patient remaining in an uncomfortable position while the dressing or paste sets up without cracking.

In addition, other antimicrobial agents such as silver nitrate or mafenide acetate (e.g., α-amino-p-toluenesulfonamide) have been used with the synthetic resin wound dressing of the present invention.

In view of the above, it will be seen that the other objects of this invention are achieved and other advantageous results obtained.

As various changes could be made in the above constructions, processes, or methods without departing from the scope of the invention, it is intended that all matter contained in the above description or shown in the accompanying drawings shall be interpreted as illustrative and not in a limiting sense.

What is claimed is:

1. In combination with a synthetic resin wound dressing of the type wherein a particulate, hydrophilic, water swellable polymer of an acrylate or acrylamide, is combined with an inert, non-toxic, water miscible organic solvent of polyethylene glycol, capable of forming a paste with said polymer, the improvement which comprises, a hydrogen bonding plasticizer of dimethylsulfoxide mixed with the combined polymer and solvent, with said polymer ranging between about 30%–55% by weight of said dressing, with said solvent ranging between about 20%–60% by weight of said dressing, and with said plasticizer being present in a plasticizing amount ranging up to about 20% by weight of said dressing.

2. A synthetic resin wound dressing of the bonding type comprising a particulate, hydrophilic, water swellable polymer of an acrylate or acrylamide, an inert, non-toxic water miscible organic solvent of polyethylene glycol, the improvement which comprises, a hydrogen bonding plasticizer mixed with said polymer and solvent, said plasticizer is a material selected from the group consisting of dimethylsulfoxide, dimethylphthalate, 2,3-butylene carbonate, dimethylformamide, dimethyltetramethylene sulfone, diethylsulfone, methylene glycolate, methylpropyl sulfone, and butyrolactone, said polymer ranging between 30%–55% by weight of said dressing, with said solvent ranging between about 20%–60% by weight of said dressing, and said plasticizer ranging up to about 20% by weight of said dressing.

3. A synthetic resin wound dressing of the preformed film type bandage comprising a particulate, hydrophilic, water swellable polymer of an acrylate or acrylamide, an inert nontoxic, water miscible organic solvent of polyethylene glycol, the improvement which comprises, a hydrogen bonding plasticizer of dimethylsulfoxide mixed with the combined polymer and solvent, said combination of polymer, solvent, and plasticizer being mixed in combination and cured to form a bandage type dressing with controlled flexibility and elasticity, and having an adherent surface, with said polymer ranging between about 30%–55% by weight of said dressing, with said solvent ranging between about 20%–60% by weight of said dressing, and with said plasticizer being present in a plasticizing amount ranging up to about 20% by weight of said dressing.

4. A synthetic resin wound dressing as set forth in claim 1, 2, or 3 and further comprising as a further ingredient a medicament agent, said medicament agent is a material selected from the group consisting of a germicide, a fungicide, an antimicrobial agent, an antibiotic, an analgesic, a hormone agent, an anti-inflammatory agent, a cardiovascular agent, an anticonvulsant agent, a pulmonary agent, and a muscle relaxant.

5. A synthetic resin wound dressing as set forth in claim 2 or 3 and wherein said dressing comprises, when said polymer, solvent, and hydrogen bonding plasticizer are mixed, a cured bandage type dressing having a controlled increased flexibility, elasticity, and surface adhesion, and which may be stored in bandage type form until usage.

6. The synthetic resin wound dressing as set forth in claim 1, 2, or 3 wherein said polymer is poly(2-hydroxyethylmethacrylate), said solvent being polyethylene glycol hving a molecular weight ranging between about 200–2000, and said hydrogen bonding plasticizer being dimethylsulfoxide with the amount of said plasticizer directly controlling the set-up of the composition in forming a substantially occlusive film, and with the length of the set-up time decreasing as the quantity of the plasticizer increases such that set-up times of less than about 30 seconds or less may be realized when the above-stated maximum quantity of said plasticizer is present, to about 45 minutes when a minimum amount of said plasticizer is present.

7. A synthetic resin wound dressing as set forth in claim 1, 2, or 3 wherein said polymer is poly(2-hydroxyethylmethacrylate).

8. A synthetic resin wound dressing as set forth in claim 7 wherein said solvent is polyethylene glycol having a molecular weight ranging between about 200–2000.

9. A synthetic resin wound dressing as set forth in claim 1, 2, or 3 wherein said bandage-type dressing comprises a substrate having a layer of said paste applied to one face thereof.

10. A synthetic resin wound dressing as set forth in claim 9 wherein said substrate is a biaxially stretchable substrate.

11. A synthetic resin wound dressing as set forth in claim 1, 2, or 3 wherein said polymer is a polymer of hydroxy($C_2$–$C_4$-alkyl)methacrylate, hydroxy($C_2$–$C_4$alkyl)acrylate, hydroxy($C_2$–$C_4$alkoxy$C_2$–$C_4$-alkyl)methacrylate,
hydroxy($C_2$–$C_4$alkoxy$C_2$–$C_4$alkyl)acrylate,
alkoxy($C_2$–$C_4$alkoxy$C_2$–$C_4$alkyl)methacrylate,
alkoxy($C_2$–$C_4$alkoxy$C_2$–$C_4$alkyl)acrylate,
N-($C_1$–$C_4$alkyl)acrylamide, N-($C_1$–$C_4$alkyl)methacrylamide,
N,N-di($C_1$–$C_4$-alkyl)acrylamide,
N,N-(di($C_1$–$C_4$alkyl)methacrylamide,
vicinal-epoxy($C_1$–$C_4$alkyl)methacrylate, or
vicinal-epoxy($C_1$–$C_4$alkyl)acrylate.

12. A synthetic resin wound dressing as set forth in claim 11 wherein said polymer is at least slightly cross-linked and has a molecular weight of at least 50,000.

13. A synthetic resin wound dressing as set forth in claim 1, 2, or 3 wherein said plasticizer is a liquid having a solubility parameter ranging between about 10.7 to about 12.6.

14. A synthetic resin wound dressing as set forth in claim 1, 2, or 3 wherein said solvent is polyethylene glycol of the general formula $H(OCH_2CH_2)_nOH$, where n is greater than or equal to 4.

15. A synthetic resin wound dressing as set forth in claim 14 wherein said polyethylene glycol solvent has a molecular weight ranging between about 200–2000, and has a boiling point of about 200° C.

16. A synthetic resin wound dressing as set forth in claim 15 wherein said polyethylene glycol has a molecular weight ranging between about 200–800.

17. A synthetic resin wound dressing as set forth in claim 4 wherein said antimicrobial agent is silver sulfadiazine.

18. A synthetic resin wound dressing as set forth in claim 17 wherein said silver sulfadiazine is present in said wound dressing ranging between about 0.5 to about 7% by weight.

19. A synthetic resin wound dressing as set forth in claim 4 wherein said cardiovascular agent is nitroglycerine.

20. A synthetic resin wound dressing as set forth in claim 19 wherein said nitroglycerine is present in said wound dressing ranging between about 0.5 to about 10% by weight.

21. A synthetic resin wound dressing as set forth in claim 4 wherein said antimicrobial agent is nitrofurazone.

22. A synthetic resin wound dressing as set forth in claim 21 wherein said nitrofurazone is present in said wound dressing ranging between about 0.5 to about 10% by weight.

23. A synthetic resin wound dressing as set forth in claim 4 wherein said antimicrobial agent is silver nitrate.

24. A synthetic resin wound dressing as set forth in claim 23 wherein said silver nitrate is present in said wound dressing ranging between about 0.5 to about 10% by weight.

25. A synthetic resin wound dressing as set forth in claim 4 wherein said antimicrobial agent consists essentially of silver sulfadiazine, nitrofurazone, or silver nitrate with the weight of said antimicrobial agent ranging between about 0.5 to about 10% by weight of said dressing.

26. A synthetic resin wound dressing as set forth in claim 4 wherein said antimicrobial agent is mafenide acetate.

27. A synthetic resin wound dressing as set forth in claim 26 wherein said mafenide acetate is present in said wound dressing ranging between about 0.5 to about 10% by weight.

28. A synthetic resin wound dressing comprising a preformed polymer film of poly(hydroxyethylmethacrylate), a solvent of polyethylene glycol, a hydrogen bonding plasticizer of dimethylsulfoxide, and a medicinal agent of silver sulfadiazine, nitrofurazone, silver nitrate, or mafenide acetate, wherein said poly(hydroxyethylmethacrylate) ranges between 30%–55% by weight of said dressing, said polyethylene glycol ranges between about 20%–60% by weight of said dressing, said dimethylsulfoxide being present in a plasticizing amount ranges up to about 20% by weight of said dressing, said medicinal agent, or combinations thereof, ranges between about 0.5% to about 10% by weight of said dressing, and wherein said composition is mixed and formed into a precured bandage type wound dressing.

29. A process of treating a wound site comprising applying a synthetic resin film type bandage wound dressing to the wound site, said wound dressing consisting essentially of a particulate hydrophilic, water swellable polymer of an acrylate or acrylamide, an inert, non-toxic, water miscible, organic solvent of polyethylene glycol, and a hydrogen bonding plasticizer, said plasticizer selected from the group consisting of dimethylsulfoxide, dimethylphthalate, 2,3-butylene carbonate, dimethylformamide, dimethyltetramethylene sulfone, diethylsulfone, methylene glycolate, methylpropyl sulfone, and butryolactone, said polymer, solvent, and plasticizer capable of forming a flexible adherent film dressing, the said polymer ranging between about 30%–55% by weight of said dressing, with said solvent ranging between about 20%–60% by weight of said dressing, and with said plasticizer being present in a plasticizing amount ranging up to about 20% by weight of said dressing.

30. The process of claim 29 wherein, said polymer, solvent, and plasticizer are initially mixed, a settable paste results which may be formed into a flexible, elastic and adherent film type bandage for application directly on the wound site.

31. The process of claim 30 further comprising applying said mixture to an adherent substrate and permitting said mixture to cure thereby to form said preformed bandage-type dressing.

32. The process of claim 30 further comprising applying said mixture to a non-adherent surface and permitting said mixture to cure thereby to form said preformed bandage-type dressing.

33. The process of claim 29 further comprising adding a medicament agent, such as a germicide, a fungicide, an antimicrobial agent, an antibiotic, an analgesic, a hormone agent, an anti-inflammatory agent, a cardiovascular agent, an anticonvulsant agent, a pulmonary agent, or a muscle relaxant.

34. The process of claim 29 wherein said plasticizer is from the group of dimethylsulfoxide, dimethylphthalate, 2,3-butylene carbonate, dimethylformamide, dimethyltetramethylene sulfone, diethyl sulfone, methylene glycolate, methyl propyl sulfone or butyrolactone.

35. The process of claim 29 wherein said polymer is poly(2-hydroxyethylmethacrylate).

36. The process of claim 35 wherein said solvent is polyethylene glycol having a molecular weight ranging between about 200–2,000.

37. The process of claim 36 wherein said plasticizer is preferably dimethylsulfoxide.

38. The process of claim 29 wherein the dressing is applied to a burn wound site.

39. The process of claim 38 wherein the dressing comprises an antimicrobial agent such as silver sulfadiazine, silver nitrate, nitrofurazone, mafenide acetate, or mixtures thereof, said antimicrobial agent ranging up to about 10% by weight of said dressing.

* * * * *